United States Patent [19]
Bublitz et al.

[11] Patent Number: 5,289,123
[45] Date of Patent: Feb. 22, 1994

[54] DETECTION OF DEFECTS IN FOOD BY DETECTING PATTERN OF CURRENT FLOW

[75] Inventors: Christopher G. Bublitz; Gour S. Choudhury, both of Kodiak, Ak.

[73] Assignee: University of Alaska, Fairbanks, Ak.

[21] Appl. No.: 820,121

[22] Filed: Jan. 14, 1992

[51] Int. Cl.[5] .................................. G01R 33/00
[52] U.S. Cl. ....................................... 324/263
[58] Field of Search .............. 324/263, 262, 228, 200, 324/692, 201, 226

[56] References Cited

U.S. PATENT DOCUMENTS

| | | | |
|---|---|---|---|
| 3,735,247 | 5/1973 | Harker | 324/227 |
| 4,969,469 | 11/1990 | Mills | 324/201 |

FOREIGN PATENT DOCUMENTS 63-9856  1/1988  Japan .................... 324/692

OTHER PUBLICATIONS

Bellingham, J. G., M. L. A. MacVicar and M. Nisenoff, "Squid technology applied to the study of electrochemical corrosion, Sea Grant Program," Massachusetts Institute of Technology, MITSG 87-6J, 1987.

Nelson, S. O. "Electrical properties of agricultural products–A critical Trans Amer. Soc. Agric. Eng." 16(2) 384–400; 1973.

Kester, Warren; "The New Tools: Cold, Hard and Objective;" Beef, Dec. 1991

Primary Examiner—Walter E. Snow
Attorney, Agent, or Firm—Finnegan, Henderson, Farabow, Garrett & Dunner

[57] ABSTRACT

A method for examining an edible product, such as fresh fish flesh, for dielectric inclusions, such as encysted parasites. The product is subjected to a current flow, which may be perturbed or deviated by any hidden inclusions. An electromagnetic effect of perturbed current flow is detected. In a preferred implementation, one or more scans of the external magnetic consequences of the effect of an inclusion allows the discovery and removal of the inclusion.

3 Claims, 9 Drawing Sheets

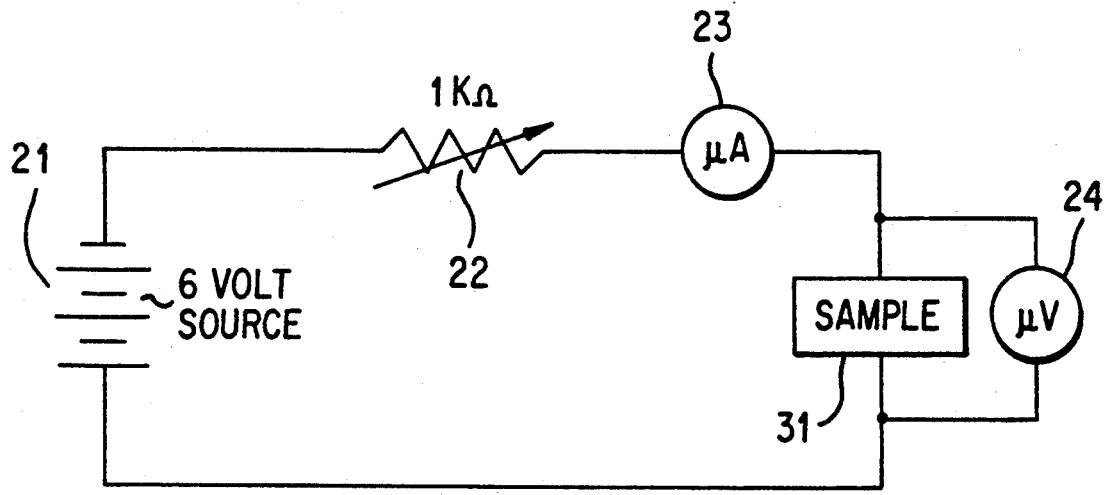
F I G. 2
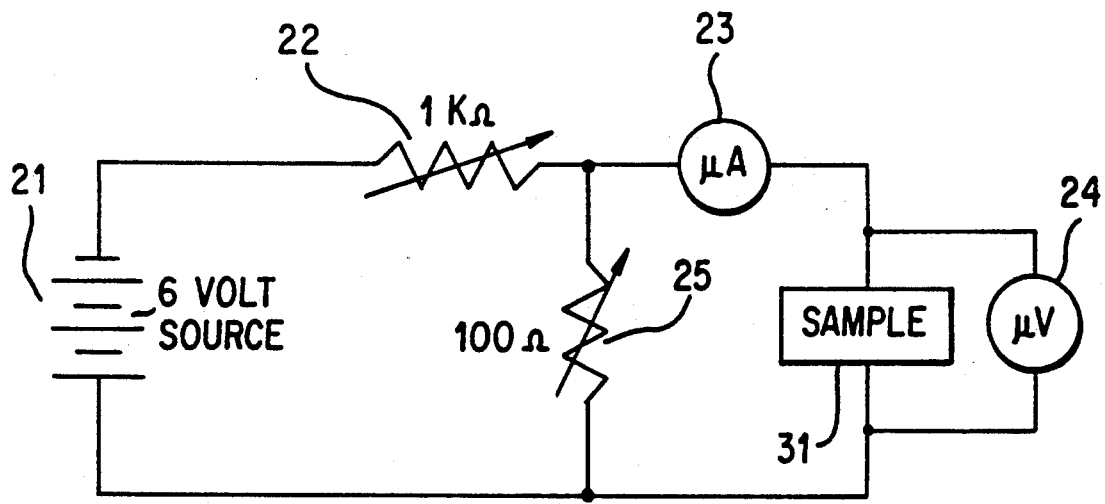
F I G. 3

FIG.5

MEASURED VALUES D-C OF ELECTRICAL CONDUCTANCE OF COD MUSCLE AND ASSOCIATED PARASITES.

| SAMPLE | WITH 100 OHM PARALLEL RESISTOR | | | | WITHOUT 100 OHM PARALLEL RESISTOR | | | |
|---|---|---|---|---|---|---|---|---|
| | V | μA | Ω | μΩ | V | μA | Ω | μΩ |
| PARASITE 1 | 0.45 | 0.5 | 900K | 0.1 | 6.0 | 23 | 261K | 0.3 |
| PARASITE 2 | 0.45 | 0.5 | 900K | 0.1 | 6.0 | 26 | 231K | 0.4 |
| FISH MUSCLE | 0.45 | 100 | 4.5K | 200 | 3.3 | 2760 | 1195 | 800 |
| TRANSVERSE PLANE | | | | | | | | |
| FISH MUSCLE | 0.5 | 100 | 5K | 200 | 3.3 | 2750 | 1200 | 800 |
| SAGITTAL PLANE | | | | | | | | |
| FROZEN TISSUE | | | | | 5.8 | 250 | 23K | 43 |
| THAWED TISSUE | | | | | 6 | 1750 | 3428 | 300 |

| FIELD STRENGTH |||
| --- | --- | --- |
| CYST DIAMETER (MM) | FIELD STRENGTH $B_B$ | RELATIVE FIELD STRENGTH $B_B/B_A$ |
| 1.0 | 0.513 | 1.025 |
| 2.0 | 0.526 | 1.053 |
| 3.0 | 0.541 | 1.081 |
| 4.0 | 0.556 | 1.111 |
| 5.0 | 0.571 | 1.143 |
| 6.0 | 0.588 | 1.177 |
| 7.0 | 0.606 | 1.212 |
| 8.0 | 0.625 | 1.250 |
| 9.0 | 0.645 | 1.290 |
| 10.0 | 0.667 | 1.333 |

FIG. 8A

| FIELD STRENGTH |||
| --- | --- | --- |
| CYST DIAMETER (MM) | FIELD STRENGTH $B_B$ | RELATIVE FIELD STRENGTH $B_B/B_A$ |
| 1.0 | 0.250 | 1.125 |
| 1.2 | 0.256 | 1.154 |
| 1.4 | 0.263 | 1.184 |
| 1.6 | 0.270 | 1.216 |
| 1.8 | 0.278 | 1.250 |
| 2.0 | 0.286 | 1.286 |
| 2.2 | 0.294 | 1.324 |
| 2.4 | 0.303 | 1.364 |
| 2.6 | 0.313 | 1.406 |
| 2.8 | 0.323 | 1.452 |
| 3.0 | 0.333 | 1.500 |

FIG. 8B

DETECTION OF DEFECTS IN FOOD BY DETECTING PATTERN OF CURRENT FLOW

BACKGROUND OF THE INVENTION

1. Field of the Invention

This invention relates to the detection of defects in food, especially fish for human consumption.

2. Discussion of the Related Art

Currently, parasite detection and removal in fish for human consumption is accomplished through visual inspection and manual removal. Detection is assisted by candling, which involves shining a light through each fillet to enhance the ability to detect embedded parasites. This method, although widely used, has several limitations. First, refraction of light by the fish musculature, especially in thick fillets, makes embedded parasites undetectable. Second, the candling process is extremely difficult to automate. Although advancements have been made, it is impossible for these systems to consistently differentiate parasites from other irregularities in the flesh. Light refraction also limits automated detection systems which utilize optical techniques. Third, worker fatigue and boredom reduces the efficiency of the detection and removal process. In addition, defects such as blood clots, bruises and discoloration also introduce inefficiencies. Consequently, candling techniques are labor-intensive and costly. It has also been found that varying light intensity and wavelength affords insufficient improvement in efficiency and may actually increase costs.

Alternatives to optical methods for detecting parasites in fish flesh have also been investigated. These techniques include ultrasonic, ultraviolet light, X-ray, sonic laser acoustic, and electronic candling. These technologies were initially developed for other applications and extensive modifications and adaptations were required for parasite detection. Application of these techniques have only marginally improved the detection efficiency over that of optical techniques. Deeply imbedded parasites may be detected by some of these procedures; however, the accuracy of detection is still limited due to the problem of pattern recognition. Thus far, no satisfactory alternative to candling has been found.

The physical state of agricultural commodities, and to some extent fishery products, has been measured using their electrical properties. See, for example, the German Offenlegungsschrift DE 3910636, published Nov. 30, 1989. Conduction of electrical energy is used for determining moisture content and to predict cooking characteristics in high-frequency dielectric or microwave heating. The Torry meter for example, uses electrical properties of fish flesh to provide a measure of fish quality. Application of electrical properties is also used extensively in the biomedical field to study the function of nerve and muscle fibers. These applications and studies have shown that DC conductivity is the most sensitive indicator of material parameters.

Nevertheless, because of the variation in size and state of fish samples that are not to be further cut up for the commercial market, it is not immediately apparent how to apply such knowledge to detect a hidden defect, such as a parasite.

SUMMARY OF THE INVENTION

This invention is based on the discovery that the conductivity of an edible, natural food, such as the conductivity of cod flesh, is more than three orders of magnitude greater than that of an encysted parasite, and that the conductivity of cod flesh is at least 2000 times greater than the conductivity of the Anisakid parasite. These differences in conductivity indicate that electrical properties of the tissue and parasite have the potential of being employed to detect embedded parasites.

It is an object of this invention to apply effectively that discovery.

Broadly, according to the invention, a method of examining an edible product includes the steps of flowing a current through the product to encompass a hidden region to be examined, and sensing an anomalous value of a pattern associated with the current flow.

In a specific, preferred implementation of the method, the steps include flowing a current through the product to encompass a hidden region to be examined and to produce a magnetic field associated with the current flow, and sensing a variation of the magnetic field that indicates a distorted path of current flow in the hidden region.

Advantageously, it has been found that both AC current and DC current can be effective, dependent in part upon the particular implementation of the invention.

Additional objects, features and advantages of the invention will be set forth in the description that follows and in part may be obvious from the description, or may be learned by practice of the invention.

The accompanying drawings, which are incorporated in and form a part of this specification, illustrate preferred implementations of the invention and, together with the description, serve to explain the principles of the invention.

BRIEF DESCRIPTION OF THE DRAWINGS

FIG. 2 is a schematic diagram of a simple form of conductivity measurement apparatus of the type used in making the discovery upon which the invention is based and useful for purposes of the invention;

FIG. 3 is a schematic diagram of a variation of the apparatus of FIG. 2, useful in a simple implementation of the invention;

FIG. 5 shows a table of measurements and calculations illustrating the discovery upon which the invention is based;

FIGS. 8A and 8B are tables showing results of calculated magnetic values along the current path in a preferred implementation for differing defects.

DETAILED DESCRIPTION OF IMPLEMENTATIONS OF THE INVENTION

Figure 1:
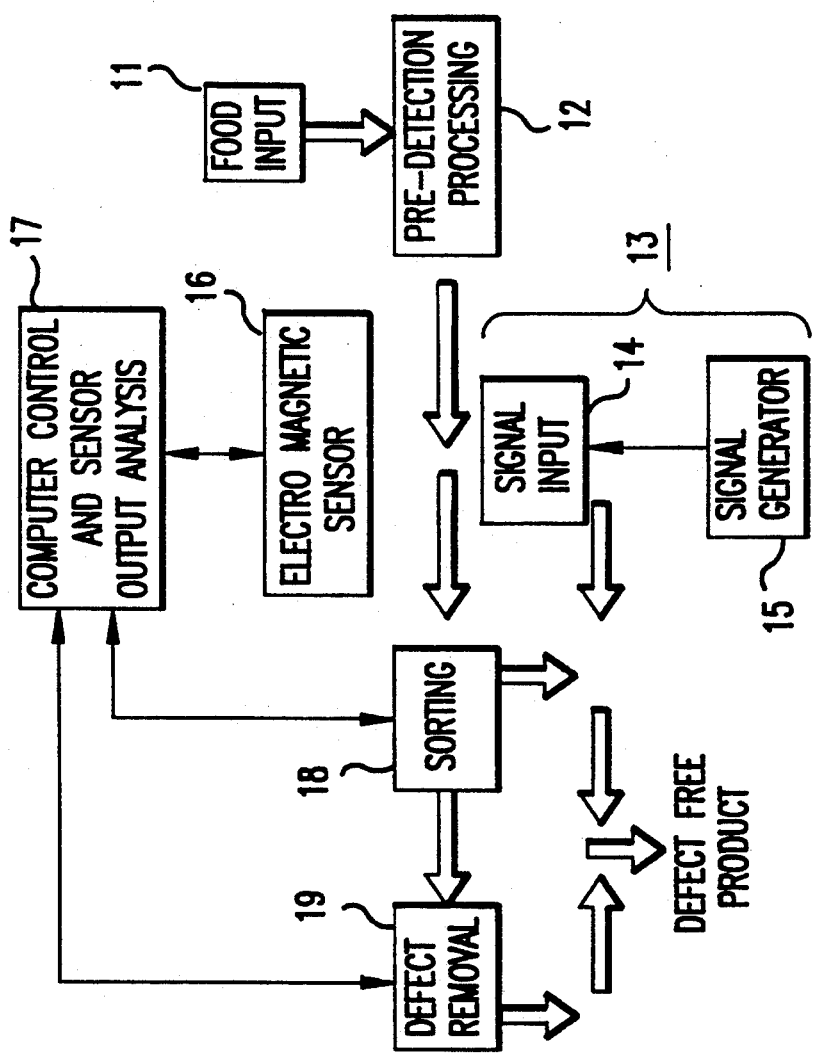
FIG. 1 is a flow diagram of an illustrative method according to the invention.

In the method according to the invention as illustrated in FIG. 1, an input stream, or series, of samples 11 is subjected to a pre-detection processing step 12. For example, fish processing operations conducted during this step include heading, gutting, and filleting of fish prior to quality control checks. Further, any dry, non-conductive rind, scale, or outer layer not desired in a commercial product can be removed in step 12.

In step 13, a signal is applied to sample 11 through clips or probes contacting sample 11 at separate points and providing terminals of a signal input 14 in response to a signal generator 15, with the net result that a current flows through each sample. In step 16, an electromagnetic property of the current flow is sensed, for example, by scanning along the sample to detect a magnetic field. In step 17, the sensed data indicating the electromagnetic property is processed by analyzing the data from step 16 and using the result to control defect removal, for example, by alerting a human operator to the location of a defect.

Prior to defect removal, defect-free product is sorted from the product stream in step 18.

It may be seen that fundamental steps of the process are those implemented in steps 13, 16, and 17. In principle, all the remaining steps could be performed by a human operator without technological assistance.

The sensing step 16 of FIG. 1 according to the invention can be further appreciated by considering FIGS. 2-3 and the discovery upon which the invention is based.

In FIG. 2, the test apparatus includes an AC or DC source 21, illustratively of 6 volts DC, a series resistor 22, which provides a current therethrough which fluctuates very little, a current-sensing device 23 in series with resistor 22 and a sample 31, and a voltage sensing device 24 in parallel with sample 31. In FIG. 3, a low resistance variable shunt 25 has been inserted to provide additional current control. By employing sample 31 which is either defect-free fresh fish flesh or Anisakid parasites, one finds that the conductivities of these materials differ by a factor of about 2000.

Figure 4:
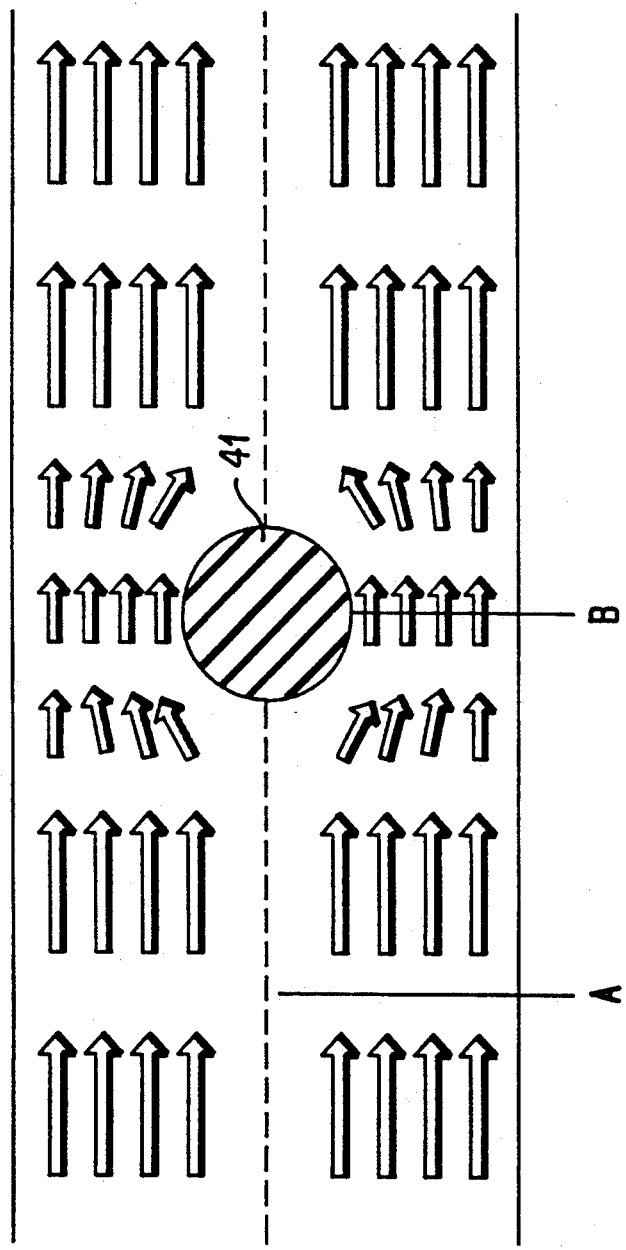
FIG. 4 is a pictorial diagram useful in explaining the principles of a preferred implementation of the invention.

To understand the relevance of FIG. 4, consider the following.

The body of a nematode, such as the Anisakid parasite, is generally divided into a number of distinct structures including an exterior cuticle; a hypodermis; a contractile and non-contractile muscular system; a pseudocoelom; and nervous, reproductive, alimentary, and excretory systems. The structure and composition of the cuticle are responsible for the large difference in conductivity between the fish flesh and parasite samples. The cuticle consists of three distinct regions comprised of nine separate layers. The surface of the cuticle is covered by a thin layer of lipid material. The outer region of the cuticle is made up of collagen and keratin; this region may also contain polyphenol oxidase and a quinone protein. The matrix of the cuticle contain both albumin and fibrous proteins similar in structure to fibrion and elastin. This region also contains small amounts of carbohydrate, lipid and some esterase enzymes. The fiber layers of the cuticle are primarily made up of collagen.

The lipid material on the exterior of the cuticle surface is non-polar and hydrophobic in nature. This material, therefore, has a high resistance and a resultant low conductivity. In addition to the external lipid material, other components of the subsurface layers of the cuticle also exhibit high resistance. These materials include keratin, carbohydrates, and lipids.

It is well known that magnetic fields are associated with current flow. Preliminary work has also shown that cod tissue is a good conductor of DC electrical current. Other experiments with dielectric heating have also shown this to be true for AC current. See the article by S. O. Nelson, "Electrical Properties of Agricultural Products—A Critical Review", *Transactions of American Society of Agricultural Engineering*, Vol. 16, No. 2, (1973), pp. 384–400. Consequently, sufficient current should flow through the cod tissue to produce an appreciable associated magnetic field. The magnetic field strength will depend on the magnitude and spatial distribution of the current flow. Current flow structure is a function of the nature and geometry of the electrodes, the electrolyte, and the geometry of the conducting material. The lack of current flow through the parasite should, therefore, distort the magnetic field in the region around the parasite.

)/Based on Ampere's Law ($\int Bdl = \mu_o i$) it is known that the magnetic field strength of a conductor is dependent upon current flow (i), magnetic permeability ($\mu_o$), and distance from the current (dl). This relationship can be evaluated for concentric circles centered on the current flow by converting Ampere's Law to the equality $B = \mu_o i / 2\pi r$, where r is the radius of each concentric circle. For each fillet the magnetic permeability and current flow will be constant. This relationship, therefore, reduces to $B = 1/r$, indicating the magnetic field strength is inversely proportional to the distance from the current flow.

The theoretical change in the magnetic field strength around a parasite embedded in fish flesh can be evaluated using this relationship. A circular non-conducting material embedded in a tissue section is illustrated in FIG. 4. A voltage applied across this tissue section will produce a current flow pattern which is characteristic of a parallel circuit. Consequently, the relative associated magnetic field strengths for each section of the circuit can be evaluated. Theoretically, the magnetic field strength around the non-conducting material will be increased due to the decrease in distance between the current flow and the point of detection.

The phenomenon shown in FIG. 4 leads one to a preferred sensing step for the invention. The encysted parasite or dielectric inclusion 41 is shown, for convenience, on the centerline of the current path through the sample. It is merely necessary that it cause a deviation of a part of the current path. Such deviations will cause the magnetic field (not shown) outside of the nearest surface of the sample to increase (as here) or to decrease (inclusion just under the surface) as the current seeks a more conductive path to avoid the inclusion.

Figure 7:
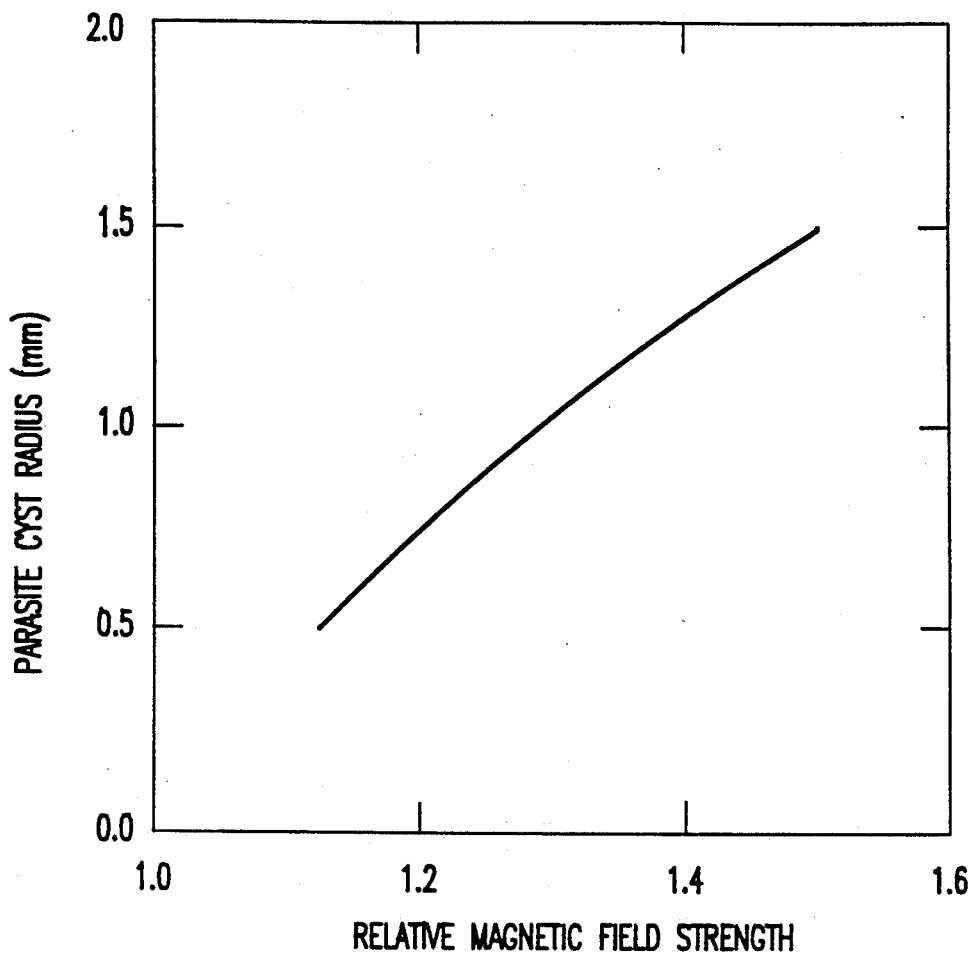
FIG. 7 is a graph useful in explaining the operation of a preferred implementation.

Assume for a moment that the shown limits of the current path are the surfaces of the sample. If each half of the tissue sample is evaluated as a separate circuit the following assumption can be made: all of the current flow through section A will pass through section B. At a point 2 cm from the tissue surface a relative magnetic field strength at A will be 0.2222 (dimensionless). Using a 1 mm diameter non-conducting area, the relative magnetic field strength at B will be 0.2500. Thus, there is a 1.125 times increase in magnetic field strength. This analysis presents a worst case scenario, i.e. the parasite is oriented lengthwise in a direction orthogonal to the current flow. Normally parasites coil or form a twisted mass when embedded. Observations during a prior parasite project indicate that embedded parasites coil at a ratio of 3:1 over random orientation. No cases have been observed where the parasite oriented either lengthwise in a horizontal or vertical direction. Consequently, as the size of the coil or mass increases the difference in relative magnetic field strength is anticipated to increase accordingly. The theoretical change in magnetic field strength associated with increasing size of the non-conducting area is given in the tables of FIGS. 8A and 8B, and is shown graphically in FIG. 7.

Figure 6:
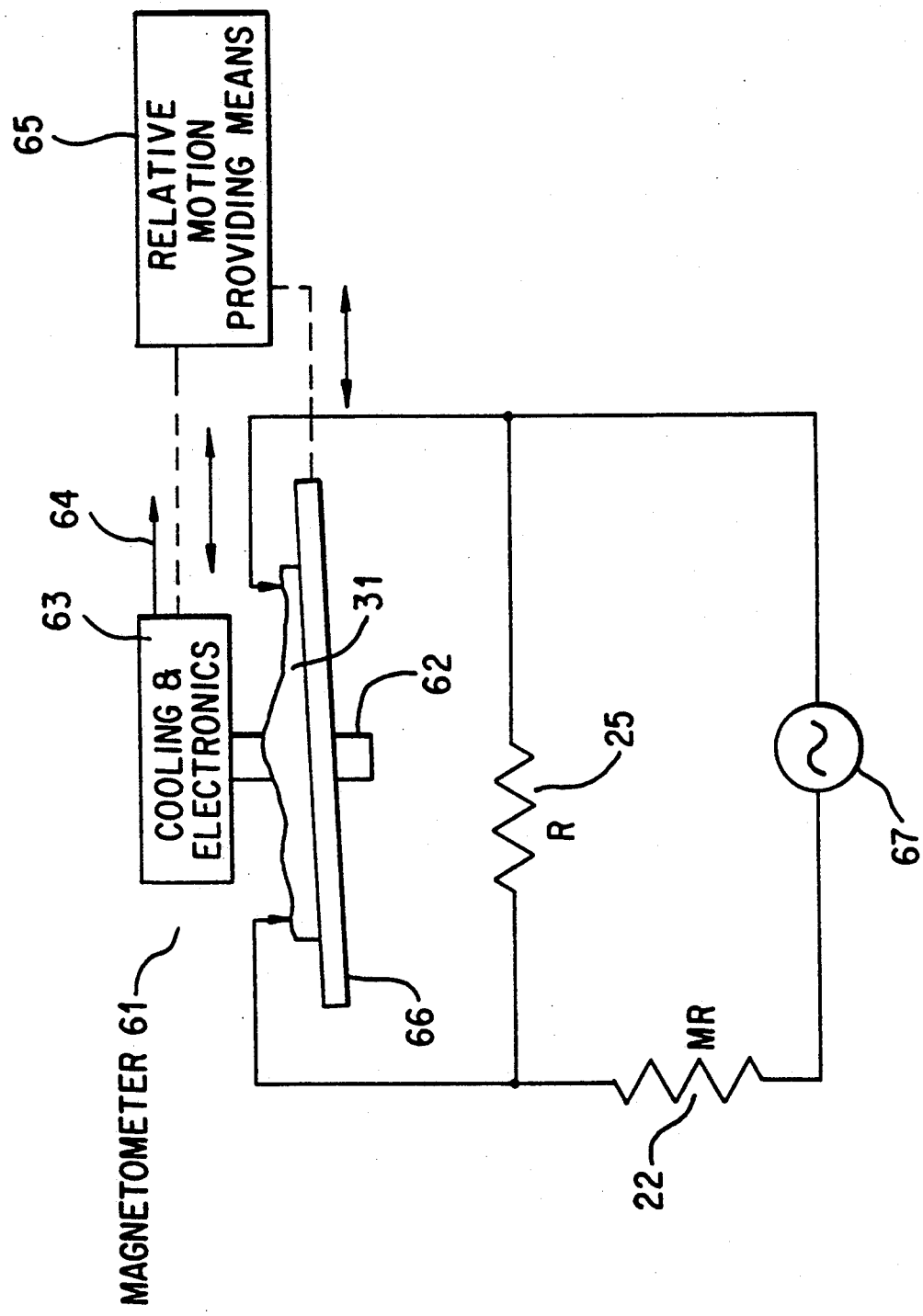
FIG. 6 is a partially schematic and partially block diagrammatic illustration of a preferred implementation of the invention.

FIG. 6 shows a magnetic field sensing implementation of the sensing step of the invention. A magnetometer 61 was used to determine the magnetic field generated by changes in induced current flow through cod fillets. Fresh and frozen infested and uninfested portions of cod fillets were tested to determine if changes in current flow patterns caused by encysted parasites could be detected. Results were plotted as a function of magnetic field strength versus relative position. See FIGS. 9A-9G as explained hereinafter.

Samples 31 were cut to a standard size of approximately 2 cm thick×2 cm wide×10 cm long. Samples were placed on a support 66 constructed of plexiglass bonded by silicone rubber. The support 66 could traverse the magnetometer detection head in measured increments in response to a relative motion providing means 65.

In principle, it makes no difference how the relative motion of sample and magnetometer is provided. In a commercial operation, the samples could be placed upon a conveyor belt, or the detection head 62 of the magnetometer 61 could traverse the sample 31.

Samples were connected to either a DC or AC constant current electrical source for analysis. A bias circuit was constructed to provide a stable voltage and current to the sample during test runs. The resulting output signals 64 can be analyzed as desired; but the analysis can be automated by computer. Results were plotted for further analysis directly from the data base to either a computer CRT or a laser printer.

Thirty-one (31) samples 31 were analyzed to determine baseline magnetic field data. These consisted of 12 samples to determine magnetic field strength associated with DC current flow and 19 samples to determine AC magnetic field strength. Graphs (not shown) of the field strength associated with DC current flow have shown less distinctive features to indicate parasite position than do analogous AC current flow versions.

The magnetic field strength curves associated with induced AC current showed several distinctive features. A standard curve was characterized by a bell shape with a plateau on either end of the curve (FIGS. 9A-9B). The shapes of these curves are not symmetrical and are dictated by coupling effects produced by the electrodes connected to the sample. The plateaus are characteristic of bare electrodes protruding beyond the end of the sample. The slopes of the curve are sharp and almost linear and a narrow peak is evident on all standard curves.

The characteristic curve shape of a defect (defect standard) was determined by embedding a non-conducting 1 cm diameter×3 mm high rubber tube into a defect-free sample. The shape of the field strength curve produced by this defect is shown in FIG. 9C. The curve is characterized by two peaks. The peak at relative position 28 (coordinate value) was characteristic of the standard bell shaped curve and was attributed to the result of the coupling effect of the sample itself. The second peak at relative position 24 is caused by the distortion in the magnetic field produced by changes in current flow patterns around the defect. The height of this peak was probably determined by the strength of the positive coupling effects. It is also probable that the shape and depth of the curve between the peaks was determined by the negative coupling effects of the magnetic field. Nevertheless, the invention is not to be limited by these tentative hypotheses.

Figure 9G:
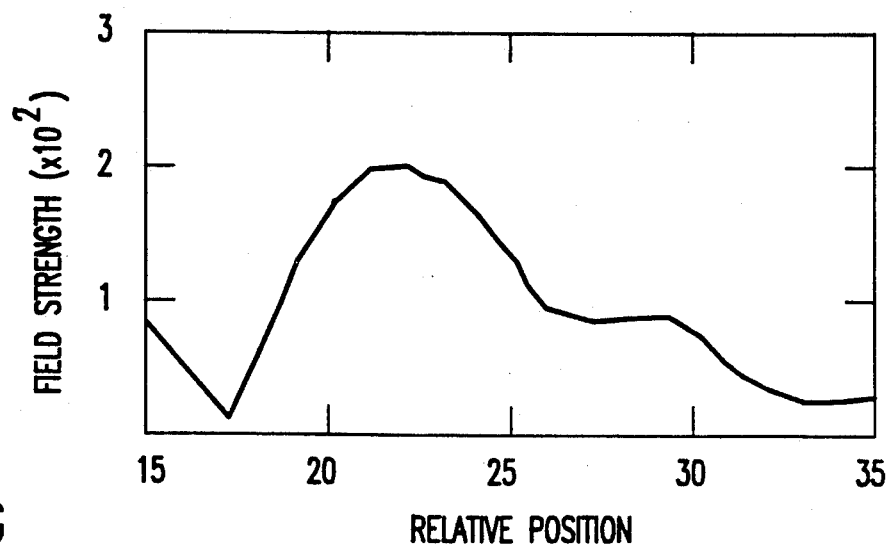
FIGS. 9A-9G show graphs of the data showing results of magnetic scans along the current path in a preferred implementation.
Figure 9A:
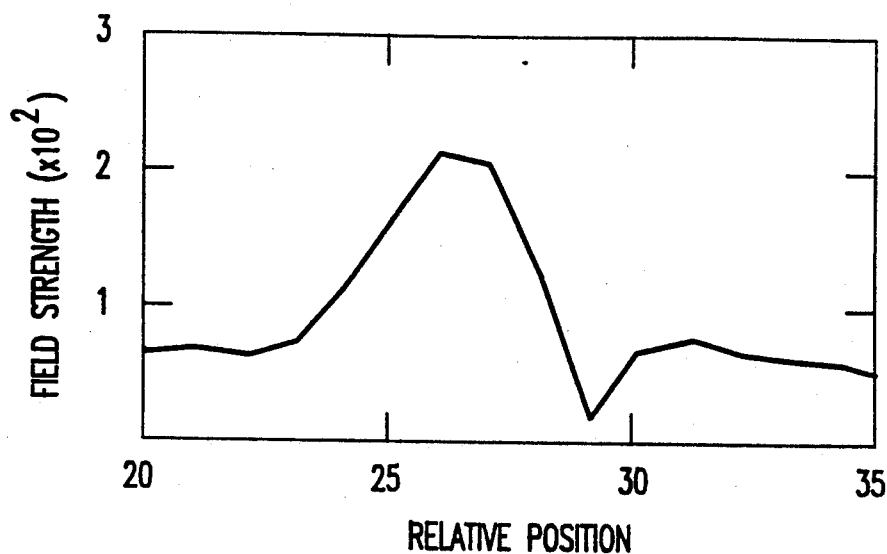
Figure 9B:
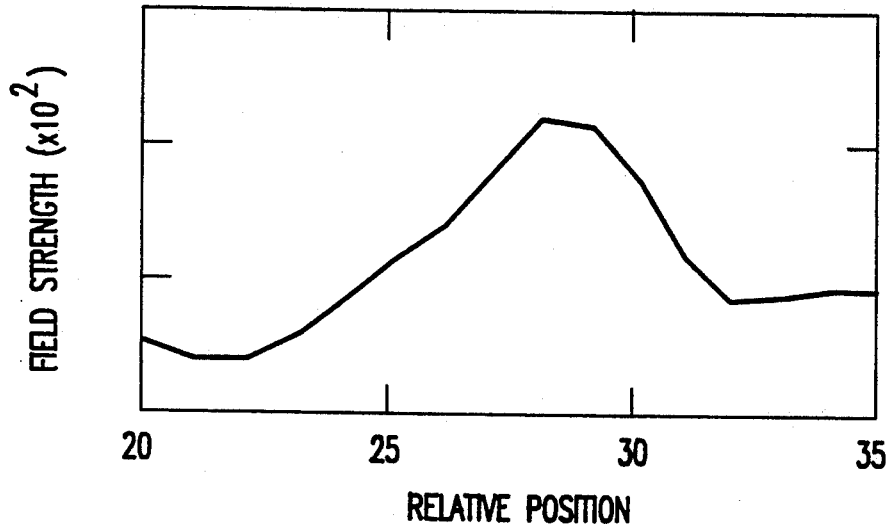
Figure 9C:
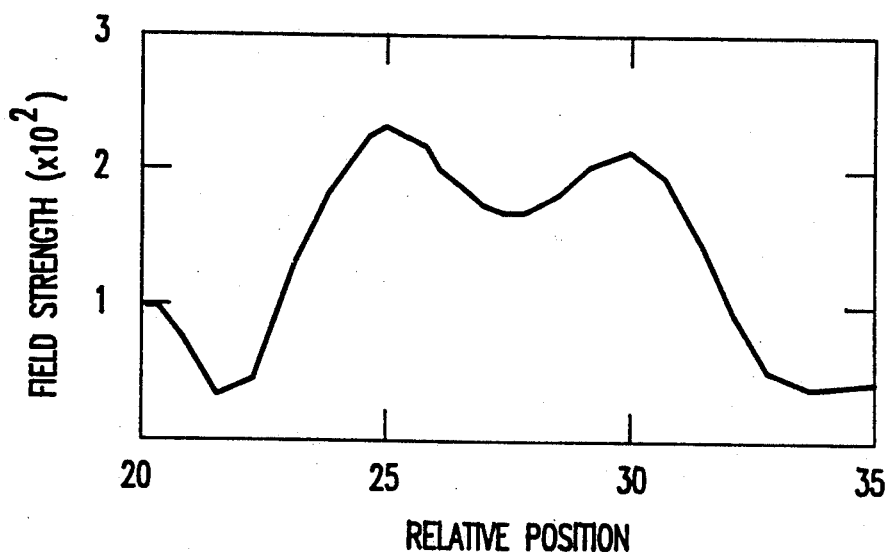
Figure 9D:
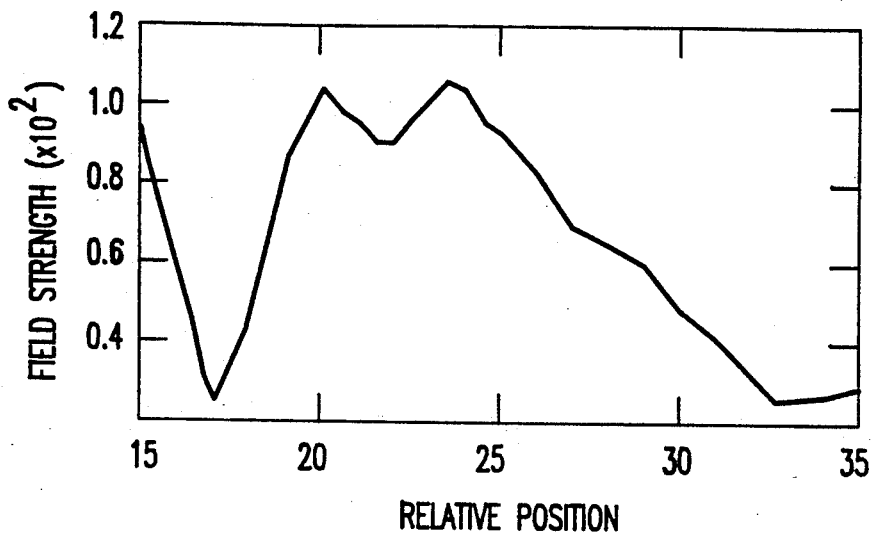

A curve profile produced by high-resistance semi-conducting tissue was determined by artificially imbedding four parasites in a defect-free sample (FIG. 9D). This curve closely resembles the shape of the defect standard curve of FIG. 9C described above. An initial peak was the result of sample coupling and a second peak was the result of defect coupling.

To determine if the effects observed for the defect standard and semi-conducting tissue were the result of the incision made to insert the defect, the incision was filled with cod flesh and tested in the same manner. Results did not indicate any field distortion produced by the incision filled with cod flesh. As a result, we concluded that the field strength curve produced by the defect standard was the result of distortions in the magnetic field caused by the higher-resistance material and not the incision.

Figure 9E:
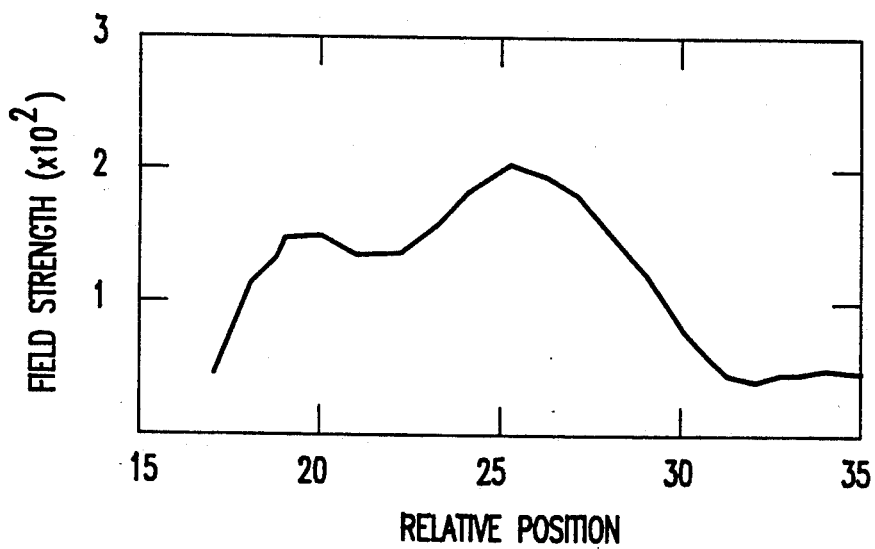

The effect on field strength of two naturally-occurring parasites embedded at relative positions 21 and 22 is shown in FIG. 9E. As with previous samples the curve shows two distinct peaks around the parasites. However, the height of the peak caused by parasite field coupling was distinctly lower than that caused by sample coupling. This was probably caused by several factors. First, the defects were naturally embedded and consequently the cod flesh was more tightly associated with the parasite. This factor would cause less pronounced disruption in current flow than a relatively large incision filled with non-conducting or semi-conducting material. Secondly, the embedded parasite coils each measured approximately 5 mm in diameter. This is one-half the size of the defects introduced to determine standard effects. Third, the two parasites were embedded in different configurations. One parasite was embedded horizontally in the flesh while the second was embedded vertically. The effects of these configurations in close proximity to each other is unknown. Finally, because the parasites were separated from each other current was able to flow through the flesh between the parasites.

Figure 9F:
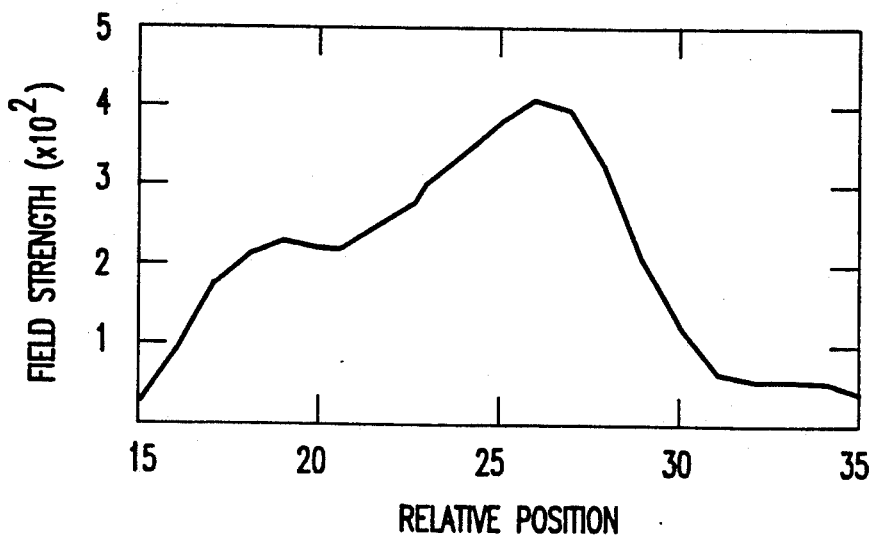

FIG. 9F shows a curve of magnetic field strength measured at relative positions similar to those of previous curves, with the difference that a sample of cod flesh included a naturally-occurring, partially embedded nematode parasite. Although a trend toward less clear definition of two peaks is seen, the peak due to the parasite at relative position 19 is still discernable and presents no problem of analysis.

FIG. 9G presents an almost mirror-image example of the magnetic field measurement for another naturally-occurring, partially embedded nematode parasite. This result might be typical for a case of an inclusion near a sample surface somewhat remote from the position of nearest approach to the detector.

In all cases, it is seen that a magnetic field scan of a food sample conducting electrical current yields a readily analyzable, double-peak indication of a dielectric (less conducting) inclusion. Moreover, inasmuch as the data results from a scan, it tends to indicate a position of the inclusion, thereby facilitating the removal steps 17 and 19 of FIG. 1. In some cases, a second scan that passes by another sample surface may eliminate ambiguity regarding location of the parasite and facilitate removal.

Even without using a magnetometer, relatively elevated values of a pattern associated with current flow in the sample can still be detected as follows. Significant variations in such a pattern, affected by the presence of a parasite, can be detected by contacting the sample with a set of four spaced-apart current probes, sequentially switching the current to flow between different pairs of the current probes, and sensing the resulting voltage drops associated with each current flow, measured between the active current probes, as in FIGS. 2 or 3.

Thus, one can detect relatively elevated values in the pattern of voltage values associated with the sequence of differently positioned current flows.

Additional advantages and modifications will readily occur to those skilled in the art. Therefore, the invention in its broader aspects is not limited to the specific details, representative devices, and illustrative examples shown and described. Accordingly, departures may be made from such details without departing from the spirit and scope of the general inventive concept as defined by the appended claims and their equivalents.

What is claimed:

1. A method of examining an edible product having a first conductivity for the presence of foreign inclusions having a second conductivity substantially different from said first conductivity, comprising the steps of:

flowing a current through the product; and detecting values of a pattern associated with the current along the flow path of the current in the product at a plurality of positions laterally disposed with respect to the flow path to indicate a relative distortion of current flow, the detecting step including one of (a) the step of employing a magnetometer and (b) the step of employing means for detecting current and voltage values.

2. The method of examining an edible product according to claim 1, wherein the detecting step includes the step of employing the magnetometer.

3. The method of claim 2, wherein the step of employing the magnetometer includes sensing magnetic field values by scanning the magnetometer along the product and detecting the presence of a selected pattern of local magnetic field variations during the scan to indicate a defect.

* * * * *

UNITED STATES PATENT AND TRADEMARK OFFICE
CERTIFICATE OF CORRECTION

PATENT NO. : 5,289,123
DATED : February 22, 1994
INVENTOR(S) : C. G. Bublitz et al.

It is certified that error appears in the above-indentified patent and that said Letters Patent is hereby corrected as shown below:

Column 1, line 3, insert

This invention was made with government support under Award No. 89-ABH-0008 of the National Oceanic and Atmospheric Administration. The government has certain rights in the invention.

Signed and Sealed this

Fifteenth Day of October, 1996

*Attest:*

BRUCE LEHMAN

*Attesting Officer*  *Commissioner of Patents and Trademarks*